US008822225B2

(12) United States Patent
Gotch et al.

(10) Patent No.: US 8,822,225 B2
(45) Date of Patent: Sep. 2, 2014

(54) METHOD OF CALCULATING A PHOSPHORUS-PROTEIN RATIO

(75) Inventors: Frank A. Gotch, San Francisco, CA (US); Amanda K. Stennett, Waltham, MA (US); Norma J. Ofsthun, Lexington, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 166 days.

(21) Appl. No.: 13/499,485

(22) PCT Filed: Oct. 1, 2010

(86) PCT No.: PCT/US2010/051155
§ 371 (c)(1), (2), (4) Date: Mar. 30, 2012

(87) PCT Pub. No.: WO2011/041697
PCT Pub. Date: Apr. 7, 2011

(65) Prior Publication Data
US 2012/0184036 A1 Jul. 19, 2012

(51) Int. Cl.
| | |
|---|---|
| *A61K 31/785* | (2006.01) |
| *A61K 31/74* | (2006.01) |
| *G01N 33/62* | (2006.01) |
| *G01N 33/84* | (2006.01) |
| *G01N 33/50* | (2006.01) |
| *G06F 19/00* | (2011.01) |
| *G01N 33/68* | (2006.01) |

(52) U.S. Cl.
CPC ............ *G01N 33/62* (2013.01); *G06F 19/3475* (2013.01); *G01N 33/84* (2013.01); *G01N 33/68* (2013.01); *A61K 31/785* (2013.01); *G01N 2800/347* (2013.01)

USPC ............... 436/43; 436/105; 436/100; 703/11; 703/6

(58) Field of Classification Search
CPC ..... A61K 31/785; A61K 31/74; A61K 31/00; G01N 33/62; G01N 33/50; G01N 33/84; G06F 19/3475
USPC ......................... 436/43, 105, 100; 703/11, 6
See application file for complete search history.

(56) References Cited

U.S. PATENT DOCUMENTS

2004/0193446 A1 9/2004 Mayer et al.

FOREIGN PATENT DOCUMENTS

WO WO 2007/130491 A2 5/2007

OTHER PUBLICATIONS

Gandara, E., et al., "Improving Adherence to Treatment Guidelines: A Blueprint," *Critical Pathways in Cardiology*, vol. 8 (4): 139-145 (2009).

Hergesell, O., et al., "Phosphate binders in uraemia: pharmacodynamics, pharmacoeconomics, pharmacoethics," *Nephrology Dialysis Transplantation*, vol. 17 (1): 14-17 (2002).

(Continued)

*Primary Examiner* — Christine T Mui
(74) *Attorney, Agent, or Firm* — Hamilton, Brook, Smith & Reynolds, P.C.

(57) ABSTRACT

A method of identifying a patient who is non-compliant with prescribed diet and/or phosphate binder regimen calculates a phosphorus-protein ratio (PPR) by calculating the patient's protein intake, measuring the patient's serum phosphorus concentration, and estimating the amount of phosphorus removed by the patient's kidneys from measured residual urea clearance. The PPR is the ratio between the total amount of phosphorus removed from the patient and the patient's protein intake. The method enables identifying a patient that is non-compliant with prescribed diet and/or phosphate binder regimen if the PPR is outside of an acceptable range.

16 Claims, 5 Drawing Sheets

(56) References Cited

OTHER PUBLICATIONS

Karamanidou, C., et al., "A systematic review of the prevalence and determinants of nonadherence to phosphate binding medication in patients with end-stage renal disease," *BMC Nephrology*, vol. 9 (2): 1-10 (2008).

Kuhlmann, Martin K., "Management of hyperphosphatemia," *Hemodialysis International*, vol. 10, (4): 338-345 (2006).

Long, C., et al., "Compliance with Dosing Guidelines in Patients with Chronic Kidney Disease," *Annals of Pharmacotherapy*, vol. 38 (5): 853-858 (2004).

Noori, N., et al., "Association of Dietary Phosphorus Intake and Phosphorus to Protein Ratio with Mortality in Hemodialysis Patients," *Clinical Journal of the American Society of Nephrology*, vol. 5 (4): 683-692 (2010).

Wang, X., et al., "Calcium and Phosphorus Balance in Chinese Continuous Ambulatory Peritoneal Dialysis Patients," *Hong Kong Journal of Nephrology*, vol. 6 (2): 92-96 (2004).

International Preliminary Report on Patentability and Written Opinion, International Application No. PCT/US2010/051155, date of mailing Apr. 12, 2012.

International Search Report and Written Opinion, International Application No. PCT/US2010/051155, date of mailing Dec. 10, 2010.

METHOD OF CALCULATING A PHOSPHORUS-PROTEIN RATIO

RELATED APPLICATION(S)

This application is the U.S. National Stage of International Application No. PCT/US2010/051155, filed Oct. 1, 2010, which designates the U.S., published in English, and claims the benefit of U.S. Provisional Application No. 61/277,935, filed Oct. 1, 2009. The entire teachings of the above applications are incorporated herein by reference.

BACKGROUND OF THE INVENTION

Phosphorus intake by a person originates from dietary sources, such as meat, dairy products and soft drinks. Protein sources account for a significant portion of phosphorus intake. See R. A. Sherman, and O. Mehta, *Dietary Phosphorus Restriction in Dialysis Patients: Potential Impact of Processed Meat, Poultry, and Fish Products as Protein Sources*, American Journal of Kidney Diseases, Vol. 54, No 1 pp. 18-23 (2009). Phosphorus (P) accumulates in patients with renal insufficiency due to lack of excretion of phosphorus by the kidney. Patients who have chronic kidney disease (CKD) stages 1-4 have some native kidney function that decreases as the disease progresses. Stage 5 is considered kidney failure, at which point some renal replacement therapy such as, for example, hemodialysis is needed. During the initial stages of CKD, patients may be able to maintain serum phosphorus concentrations within acceptable levels; however, as CKD progresses this may become more difficult, requiring the use of phosphate binder therapy. The patient is then prescribed an intake of phosphate ($PO_4$) binders, such as calcium acetate (e.g., PhosLo®) or calcium carbonate, that is intended to maintain the phosphorus concentration in the patient's blood to a normal or near normal level, typically between about 3.5 and about 5.5 mg/dL, preferably about 4.5 mg/dL. The phosphate binder converts the phosphorus ingested by the patient into a bound (phosphate) form that cannot be absorbed and is therefore eliminated from the patient's body. Additionally, patients who have started hemodialysis treatment may still have some residual native kidney function. This residual renal function will be an additional means of phosphorus removal for such patients. In order to estimate the magnitude of this removal, the amount of phosphorus contained in urine for patients with a range of residual renal function needs to be measured.

For patients with end stage renal disease (ESRD), the excess phosphorus is often not sufficiently eliminated by dialysis treatments. Consequently, nearly all ESRD patients develop hyperphosphatemia. See J. T. Daugirdas, P. G. Blake, and T. S. Ing, *Handbook of Dialysis*, (2007). Increased phosphorus levels have a significant role in the high mortality rate observed in the population of patients on long-term dialysis therapy. B. Kestenbaum, *Phosphate metabolism in the setting of chronic kidney disease: Significance and recommendations for treatment*, Semin. Dial. Vol. 20, pp. 286-294 (2007).

An ongoing challenge for patients with renal insufficiency is the daily pill burden and its relation to health-related quality of life. One study found that about half of the daily pill burden in maintenance dialysis patients is due to prescribed phosphate binders, and only 38% of the patients were adherent to the prescribed phosphate binder therapy, with a higher pill burden from phosphate binders being associated with lower adherence. Y. W. Chiu, I. Teitelbaum, M. Misra, E. M. de Leon, T. Adzize, and R. Mehrotra, *Pill burden, adherence, hyperphosphatemia, and quality of life in maintenance dialysis patients*, Clin. J. Am. Soc. Nephrol., Vol. 4, pp. 1089-1096 (2009).

Therefore, a method is needed to identify the patients that are non-compliant with a prescribed diet and/or a phosphate binder regimen, in order to aid the physician in making clinical decisions.

SUMMARY OF THE INVENTION

The invention generally is directed to a method of identifying a patient who is non-compliant with a prescribed diet and/or a phosphate binder regimen causing hyperphosphatemia in the patient.

In one embodiment, the method of identifying a patient who is non-compliant with a prescribed diet and/or a phosphate binder regimen over a defined time interval prior to a medical treatment in which phosphorus is removed from the patient includes determining the patient's protein intake over said defined time interval, determining the amount of phosphorus removed from the patient during said defined time interval and said medical treatment, calculating a ratio between the amount of phosphorus removed from the patient during said defined time interval and said medical treatment and the patient's protein intake over said defined time interval, and identifying a patient that is non-compliant with a prescribed diet and/or a phosphate binder regimen if the ratio is outside of an acceptable range. In some embodiments, determining the amount of phosphorus removed from the patient during said defined time interval and said medical treatment comprises measuring the patient's serum phosphorus concentration before and after said medical treatment to determine the amount of phosphorus removed from the patient by said medical treatment, estimating the amount of phosphorus removed by the patient's kidneys during said defined time interval, determining the amount of phosphorus that would be removed from the patient by the prescribed binder regimen, and adding these amounts. The medical treatment can include dialysis treatment. Alternatively, the medical treatment can be hemofiltration, or hemodiafiltration. Estimating the amount of phosphorus removed by the patient's kidneys can be based upon the patient's measured residual urea clearance. The phosphate binder regimen can include ingestion of phosphate binder tablets or gelcaps. The defined time interval can be the time interval between the end of one dialysis treatment and the beginning of the next subsequent dialysis treatment. Determining the patient's protein intake can include an in vitro measurement of blood urea nitrogen concentration using an automated clinical chemistry analyzer. Measuring the patient's serum phosphorus concentration can include an in vitro measurement using an automated clinical chemistry analyzer.

In another embodiment, the method includes a calculation of a phosphorus-protein ratio (PPR) by calculating the patient's protein intake, measuring the patient's serum phosphorus concentration, and estimating the amount of phosphorus removed by the patient's kidneys from measured residual urea clearance, and removed by dialysis (if the patient is undergoing dialysis) and by phosphate binder therapy. The PPR is the ratio between the total amount of phosphorus removed from the patient and the patient's protein intake. The method enables identifying a patient that is non-compliant with a prescribed diet and/or a phosphate binder regimen if the PPR is outside of an acceptable range. In some embodiments, the acceptable range of the PPR is between about 8 and about 14. In embodiments in which the patient is undergoing dialysis treatment, the patient's serum phosphorus concentration is measured before and after the dialysis treatment. In these embodiments, the total amount of phosphorus removed from the patient includes an amount removed by the dialysis treatment and an amount removed by the prescribed phosphate binder intake.

In yet another embodiment, a computer system for identifying a patient who is non-compliant with a prescribed diet and/or a phosphate binder regimen over a defined time interval prior to a medical treatment in which phosphorus is removed from the patient includes a user input means for determining patient data from a user, a digital processor coupled to receive determined patient data from the input means, wherein the digital processor executes a modeling system in working memory, wherein the modeling system determines the patient's protein intake over said defined time interval, determines the amount of phosphorus removed from the patient during said defined time interval and said medical treatment, calculates a ratio between the amount of phosphorus removed from the patient during said defined time interval and said medical treatment and the patient's protein intake over said defined time interval, and identifies a patient that is non-compliant with a prescribed diet and/or a phosphate binder regimen if the ratio is outside of an acceptable range. The computer system further includes an output means coupled to the digital processor, the output means provides to the user the ratio between the phosphorus removed from the patient and the patient's protein intake.

This invention has many advantages, including providing quantitative information to physicians regarding patient compliance with a prescribed diet and/or phosphate binder regimen.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

The PPR modeling system and the method of identifying a patient who is non-compliant with a prescribed diet and/or phosphate binder regimen includes a calculation of a phosphorus-protein ratio (PPR). The denominator in the PPR is the patient's protein intake, typically expressed in grams/day. For a patient undergoing dialysis treatment, the measured quantities can be determined from in vitro measurements of the patient's pre- and post-dialysis blood urea nitrogen (BUN) concentration levels, typically expressed in mg/dL (milligrams/deciliter) and measured using an automated clinical chemistry analyzer. Urea is the major end product of protein catabolism, making up about 90% of waste nitrogen accumulating in body water between dialysis treatments. Measuring the amount of urea removed by dialysis yields an estimate of the protein catabolic rate (PCR), typically expressed in grams/day. PCR is used as an estimate of the patient's dietary protein intake when the patient is in a stable state, that is, neither building up muscle mass, nor wasting away due to other health issues. The BUN is a concentration, typically expressed in mg/dL, however, and therefore the other variable required to obtain the grams of urea and hence grams of protein intake by the patient is the volume of distribution of urea in the patient's body. The volume of distribution is obtained from urea kinetic modeling (UKM), which takes into account the movement of urea from poorly perfused areas (such as the arms and legs) to the extracellular space, after dialysis has been completed. This volume of distribution is called the double pool or equilibrated volume of distribution, and the end result is called the equilibrated protein catabolic rate (ePCR). See T. Depner, and J. Daugirdas, *Equations for normalized protein catabolic rate based on two-point modeling of hemodialysis urea kinetics*, Journal of the American Society of Nephrology, Vol. 7 (5), pp. 780-785 (1996). For a patient that is not undergoing dialysis treatment, such as, for example, a CKD patient, the total intake of protein by the patient can be measured from a log of what the patient ate over the defined time interval, which can be, for example, the time interval between dialysis treatments.

Figure 1:
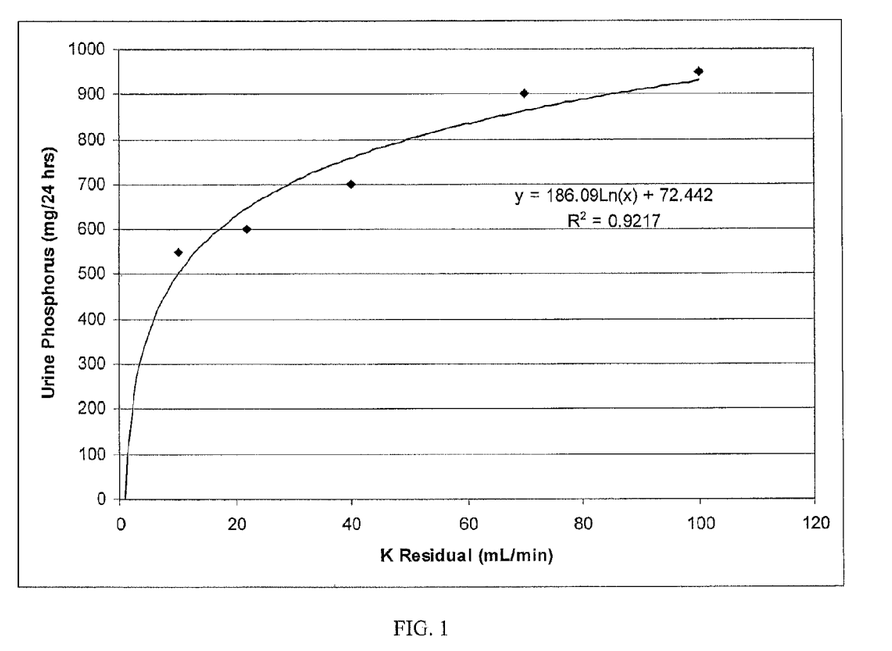
FIG. 1 is a graph of phosphorus removed by kidney as a function of residual renal clearance, based on the Craver et al., data cited below.

The numerator of the PPR can have several additive components. The first component can be the estimate of the amount of phosphorus removed by the patient's kidneys from measured residual urea clearance, if any. The amount of phosphorus contained in urine for patients with a range of residual renal function must be known in order to estimate the magnitude of the amount of phosphorus removed. Craver et al. analyzed 24 hour urine samples for total phosphorus for patients with CKD stages 1-5. L. Craver, M. P. Marco, I. Martinez, M. Rue, M. Borras, M. L. Martin, F. Sarro, J. M. Valdivielso, and E. Fernandez, *Mineral metabolism parameters throughout chronic kidney disease stages 1-5-achievement of K/DOQI target ranges*, Nephrol. Dial. Transplant, Vol. 22, pp. 1171-1176 (2007). Correlating this phosphorus amount with residual renal clearance yields a relationship, illustrated in FIG. 1, that can be used to estimate the phosphorus removal by the kidneys of patients whose residual renal clearance has been measured. When this residual renal clearance is known, the additional amount of phosphorus removed can be included in the total amount of phosphorus removed from the patient. For a patient undergoing dialysis treatment, residual renal function can be calculated from measuring the volume of urine collected between dialysis treatments, the urine BUN concentration, and the pre- and post-dialysis treatment serum BUN concentrations. The residual renal function, Kru, can be obtained from $$Kru = [(\text{Urine BUN})*(\text{urine volume})]/[(\text{average of (pre- and post-BUN)})*(\text{time between dialyses})] \quad (1)$$

For a patient that is not undergoing hemodialysis treatment (e.g., CKD or peritoneal dialysis patients), residual renal function can be calculated from measuring the volume of urine collected over a specific time period (e.g., 24 hours), the urine BUN concentration, and a serum BUN concentration. The residual renal function, Kru, can be obtained from $$Kru=[(\text{Urine BUN})*(\text{urine volume})]/[(\text{serum BUN})*(\text{collection time})] \quad (2)$$

The second component of the numerator of the PPR, for a patient that is undergoing dialysis treatment, is the amount of phosphorus removed by dialysis. The measured quantities are the pre- and post-dialysis treatment serum phosphorus concentrations. Phosphorus in human serum, plasma, or urine can be quantitatively determined in vitro using an automated clinical chemistry analyzer. The method employed by the analyzer can be photometric. For example, inorganic phosphate will form an ammonium phosphomolybdate complex having the formula $(NH_4)_3 [PO_4(MoO_3)_{12}]$ with ammonium molybdate in the presence of sulfuric acid. The concentration of the complex can be determined photometrically in the ultraviolet region (340 nm). R. J. Henry, *Clinical Chemistry: Principles & Techniques*, $2^{nd}$ Ed. p. 723 (1974).

The amount of phosphorus removed by the hemodialysis treatment, P_HD, typically expressed in milligrams (mg), can be obtained from $$P\_HD=(-(D\_P*(1-Q\_f/Q\_pw)+Q\_f)*C\_P\_m)* \text{DIAL\_TIME}/100 \quad (3)$$

where D_P is the dialysance of phosphorus of the dialyzer, typically expressed in mL/min, Q_f is the ultrafiltration rate, typically expressed in mL/min, Q_pw is the plasma water flow rate, typically expressed in mL/min, C_P_m is the mean serum phosphorus concentration, typically expressed in mg/dL, and DIAL_TIME is the dialysis treatment time, typically expressed in minutes.

The dialysance of phosphorus of the dialyzer can be obtained from $$D\_P=Q\_pw*(1-\exp[(300/Q\_pw)*(1-Q\_pw/\text{DI-ALYSATE\_FLOW})])/(Q\_pw/\text{DIALYSATE\_FLOW}-\exp[(300/Q\_pw)*(1-Q\_pw/\text{DIALY-SATE\_FLOW})]) \quad (4)$$

where the DIALYSATE_FLOW is the flow rate of the dialysate through the dialyzer, typically expressed in mL/min. The ultrafiltration rate, Q_f, can be obtained from $$Q\_f=UF\_t*1000/\text{DIAL\_TIME} \quad (5)$$

where UF_t is the total ultrafiltration volume, typically measured in liters (L). The total ultrafiltration volume can be obtained from pre- and post-treatment weights of the patient and the total fluid volume administered during the dialysis treatment as $$UF\_t=\text{WEIGHT\_PRE}+\text{TOTAL\_FLUIDS}/1000-\text{WEIGHT\_POST} \quad (6)$$

where WEIGHT_PRE is the patient's weight before the dialysis treatment, TOTAL_FLUIDS is the volume of fluids administered during the dialysis treatment, typically expressed in mL, and WEIGHT_POST is the patient's weight after the dialysis treatment.

The plasma water flow rate, Q_pw, can be obtained from $$Q\_pw=0.94*\text{BLOOD\_FLOW}*(1-H/100) \quad (7)$$

where BLOOD_FLOW is the blood flow rate through the dialyzer, typically expressed in mL/min, and H is the hematocrit fraction of the blood, typically expressed in percent.

The mean serum phosphorus concentration, C_P_m, can be obtained from $$C\_P\_m=C\_P\_0*(1-(1-1.1*(C\_P\_t/C\_P\_0))*(1-\exp(-1.73*KtV\_P))) \quad (8)$$

where C_P_0 is the patient's serum phosphorus concentration pre-treatment, C_P_t is the patient's serum phosphorus concentration post-treatment, and KtV_P is the phosphorus dialysis adequacy of the dialyzer. The KtV_P is a unitless measure of the effectiveness of phosphorus removal by dialysis. The KtV_P can be obtained from $$KtV\_P=((D\_P*\text{DIAL\_TIME})/(\text{MEAN\_VOLUME}/3))/1000 \quad (9)$$

where MEAN_VOLUME is the mean kinetic urea volume of distribution, typically expressed in liters, and obtained from UKM.

The daily average change in phosphorus due to hemodialysis, P_HD_d, can be obtained from $$P\_HD\_d=P\_HD*N\_tx/7 \quad (10)$$

where N_tx is the number of dialysis treatments the patient undergoes per week.

The third component of the numerator of the PPR is the amount of phosphorus that would be removed from the patient by the prescribed number of phosphate binder pills. The total amount of phosphorus removed from the patient, which should equal the patient's total dietary intake of phosphorus, P_di, can be obtained from $$P\_di=(-P\_HD\_d/0.75)+25*N\_PL+(186*\text{Ln}(Kru)+72) \quad (11)$$

where N_PL is the number of PhosLo® phosphate binder pills prescribed to the patient. PhosLo® typically removes 25 mg of phosphorus per pill (Fresenius Medical Care North America, Waltham, Mass.). Hereinafter, the dosage of PhosLo® is 667 mg per pill unless otherwise noted. Equation 11 includes the patient's residual renal function, Kru, which can be set to zero if it is unknown for a particular patient.

The phosphorus-protein ratio can be obtained from $$PPR=P\_di/\text{EQUILIBRATED\_PCR} \quad (12)$$

The PPR is the ratio between the total amount of phosphorus removed from the patient, P_di, and the patient's protein intake, EQUILIBRATED_PCR (ePCR). The PPR enables the identification of a patient that is non-compliant with prescribed diet and/or phosphate binder regimen if the PPR is outside of an acceptable range. In some embodiments, the acceptable range of the PPR is between about 8 and about 14. A PPR higher than about 14 indicates, for example, that the patient is non-compliant with the prescribed binder regimen, that is, the patient is not actually taking enough binder pills, and therefore the amount of phosphorus removed during the dialysis treatment is larger than would be expected for the binder prescription. A PPR lower than about 8 indicates that either the patient is not getting the expected amount of phosphorus per gram of protein intake, or the patient has some residual renal function that is not being accounted for.

Figure 6:
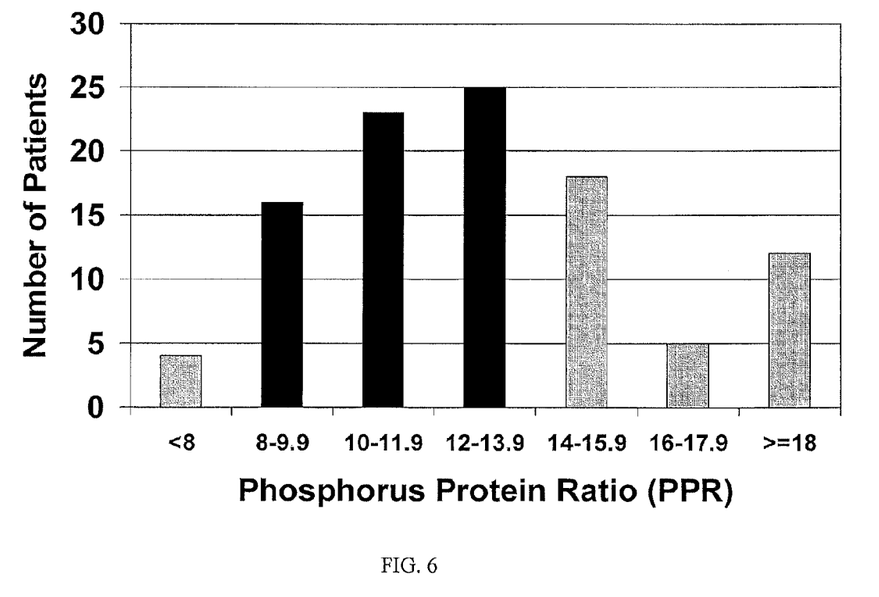
FIG. 6 is a graph of a PPR distribution among a group of 103 patients illustrating that about 64% of the patients had a PPR in the recommended range of between about 8 and about 14, about 24% of the patients had a PPR in a range of between about 14 and about 18, indicating possible non-compliance, and about 12% of the patients had a PPR above 18, indicating likely/severe non-compliance with a prescribed diet and/or phosphate binder regimen.

As shown in FIG. 6, a PPR distribution among a group of 103 patients studied revealed that about 64% of the patients had a PPR in the recommended range of between about 8 and about 14, about 24% of the patients had a PPR in a range of between about 14 and about 18, indicating possible non-compliance, and about 12% of the patients had a PPR above 18, indicating likely/severe non-compliance with a prescribed diet and/or phosphate binder regimen. After an identification of a possible non-compliance, treatment options include adjusting the patient's binder regimen or diet, or adjusting the make-up of the dialysate for the patient's dialysis treatment.

Figure 7:
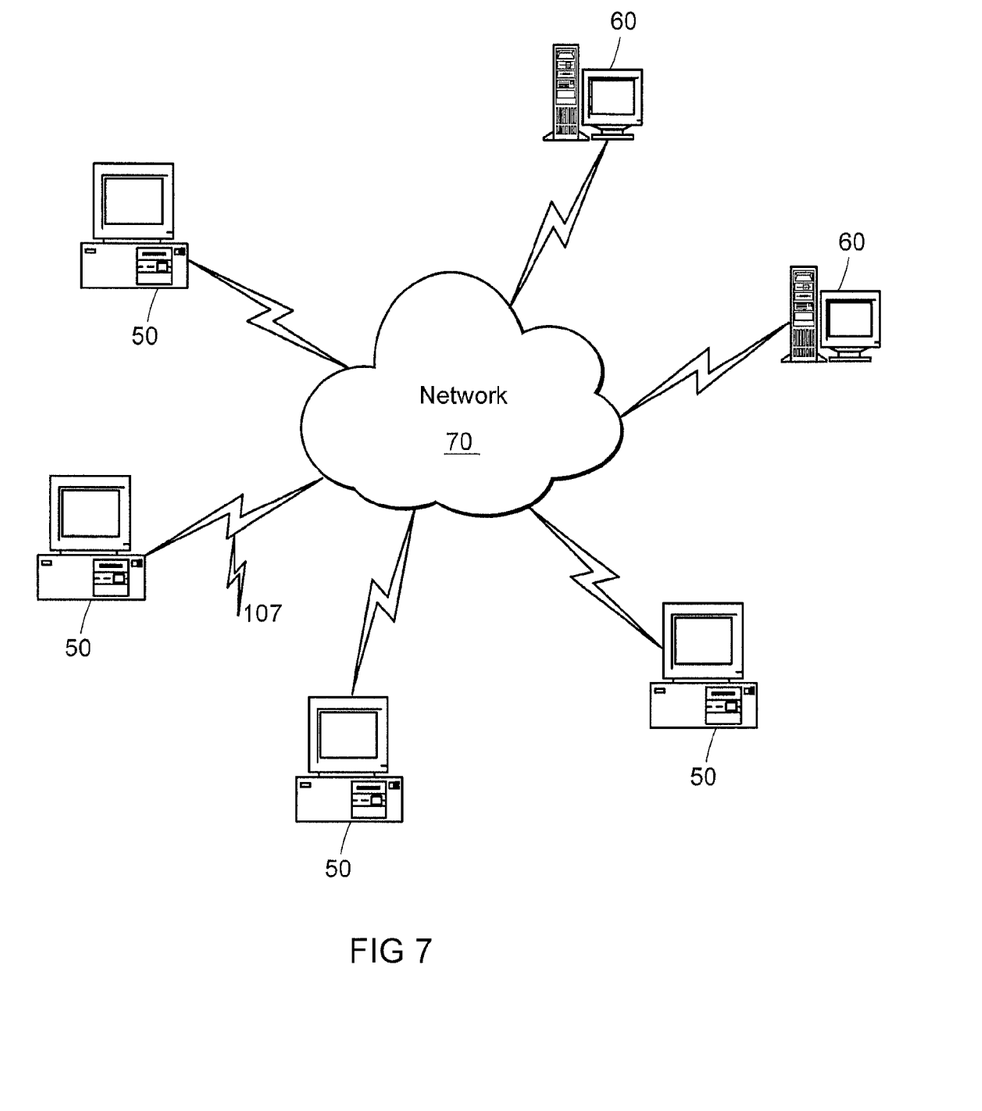
FIG. 7 is a schematic view of a computer network in which the present invention may be implemented.

FIG. 7 illustrates a computer network or similar digital processing environment in which the present invention can be implemented.

Client computer(s)/devices 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

Figure 8:
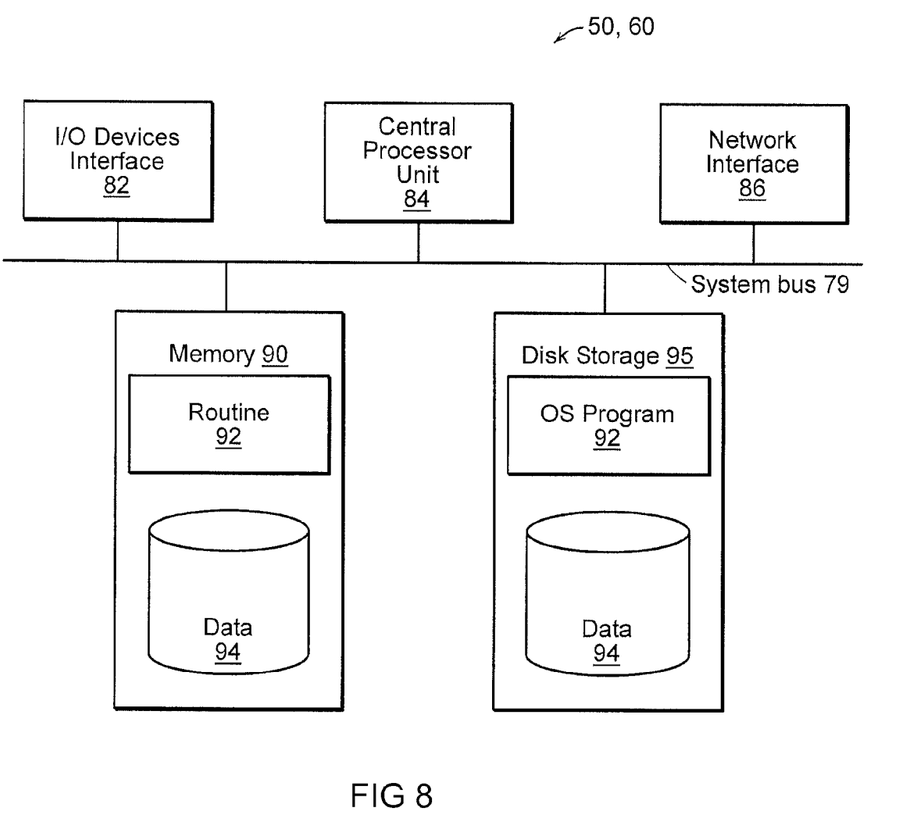
FIG. 8 is a block diagram of a computer of the network of FIG. 7.

FIG. 8 is a diagram of the internal structure of a computer (e.g., client processor/device 50 or server computers 60) in the computer system of FIG. 7. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 7), Memory 90 provides volatile storage for computer software instructions 92 and data 94 used to implement an embodiment of the present invention. All of the data 94 required for the calculations of phosphorus removed, protein catabolic rate, and the final PPR (i.e., Eqs. 1-12 detailed above) can be stored in a clinical data system, for example Proton (Clinical Computing, Inc., Cincinnati, Ohio). This clinical data from various computers on a network can be compiled in a relational database, for example Oracle database (Oracle Corp., Redwood Shores, Calif.). A program such as Microsoft Access can be used to extract required clinical data from the Oracle database and perform required calculations. Alternatively, the data extracted in the Microsoft Access can be exported to a spreadsheet program, such as Microsoft Excel, to perform the required calculations. Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 can receive and read, such as by receiving the propagation medium and identifying a propagated signal embodied in the propagation medium, as described above for computer program propagated signal product.

Generally speaking, the term "carrier medium" or "transient carrier" encompasses the foregoing transient signals, propagated signals, propagated medium, storage medium and the like.

EXEMPLIFICATION

Example 1

Figure 2:
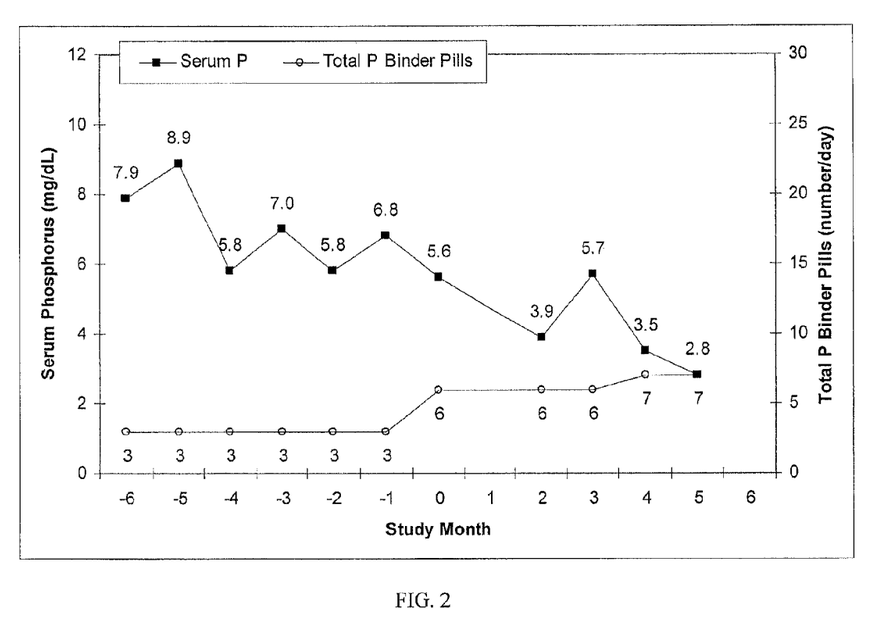
FIG. 2 is a graph of serum phosphorus concentration and number of prescribed phosphorus binder pills for Patient 1.

Patient 1 was a 53 year old diabetic, African-American male with a dialysis vintage of 19 months. Prior to use of the PPR, the 6-month, 3-month, and 1-month average serum P was 7.0, 6.5, and 6.8 mg/dL, respectively. All of these values are outside the recommended guidelines of 3.5-5.5 mg/dL. In the 6 months prior to the study, Patient 1 was prescribed 3 (800 mg) RENAGEL®, sevelamer hydrochloride, tablets per day. Once per month for 6 months (study months 0-5), input values were collected for the PPR and recommended binder prescription and dialysate calcium concentrations were calculated. As illustrated in FIG. 2, during the study period, Patient 1's binder prescription was increased to 6 and then 7 PhosLo® pills per day in order to bring serum P level down to the recommended guidelines. For the 6 month study period, average serum P was 4.0 mg/dL. Serum P fell within recommended guidelines for the study period. The average PPR for Patient 1 during the study period was 6.7. Clinical staff were alerted to monitor accuracy of P binder prescription and intake of quality protein.

Example 2

Figure 3:
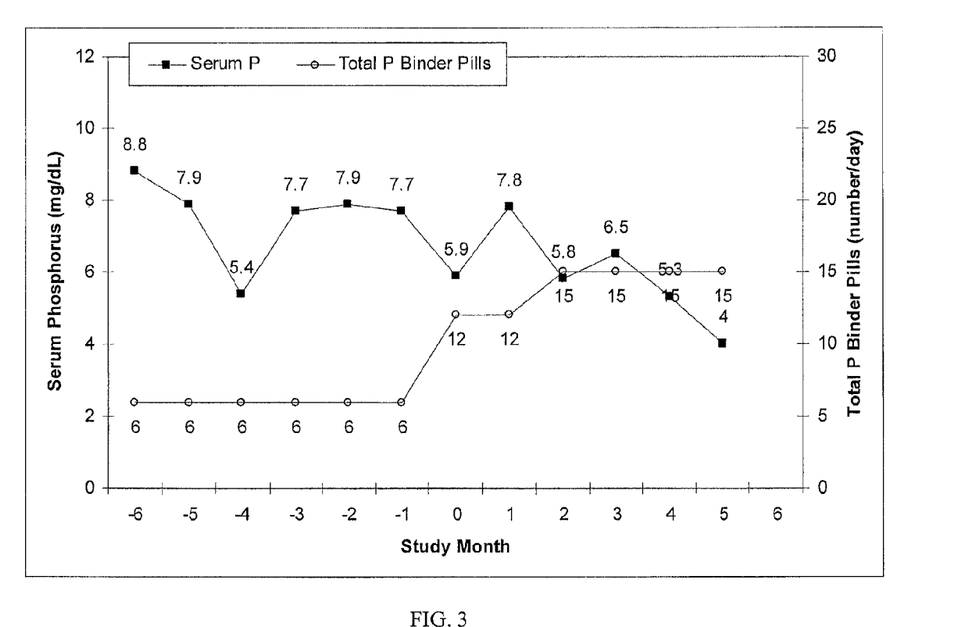
FIG. 3 is a graph of serum phosphorus concentration and number of prescribed phosphorus binder pills for Patient 2.

Patient 2 was a 61 year old African-American male with a dialysis vintage of 41 months. Prior to use of the PPR, the 6-month, 3-month, and 1-month average serum P was 7.6, 7.8, and 7.7 mg/dL, respectively. All of these values are outside the recommended guidelines of 3.5-5.5 mg/dL. In the 6 months prior to the study, Patient 2 was prescribed 6 PhosLo® tablets per day. Once per month for 6 months (study months 0-5), input values were collected for the PPR and recommended binder prescription was calculated. As illustrated in FIG. 3, during the study period, Patient 2's binder prescription was increased to 12 and then 15 PhosLo® pills per day in order to bring serum P level down to the recommended guidelines. For the 6 month study period, average serum P was 5.9 mg/dL. Average serum P fell by 22% although did not meet target guidelines. The average serum P for the last 3 months of the study was 5.3 mg/dL. Continued observation in the study would likely continue to result in serum P value within the recommended guidelines. The average PPR for Patient 2 during the study period was 13.9, which was within the recommended range.

Example 3

Figure 4:
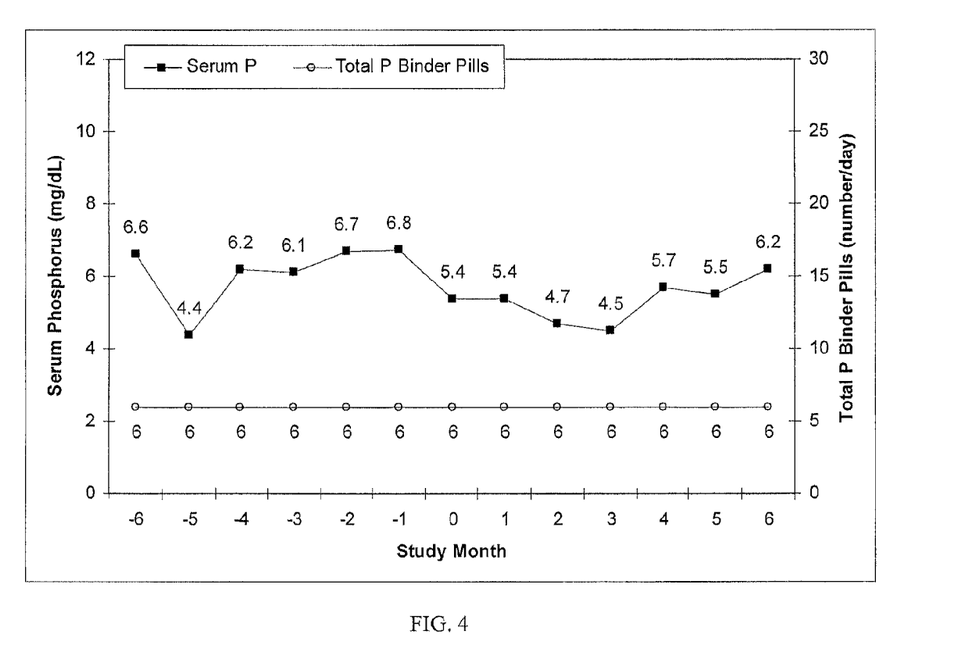
FIG. 4 is a graph of serum phosphorus concentration and number of prescribed phosphorus binder pills for Patient 3.

Patient 3 was a 72 year old diabetic, white female with a dialysis vintage of 22 months. Prior to use of the PPR, the 6-month, 3-month, and 1-month average serum P was 6.2, 6.6, and 6.8 mg/dL, respectively. All of these values are outside the recommended guidelines of 3.5-5.5 mg/dL. In the 6 months prior to the study, Patient 3 was prescribed 6 PhosLo® tablets per day. Once per month for 7 months (study months 0-6), input values were collected for the PPR and recommended binder prescription was calculated. As illustrated in FIG. 4, during the study period, Patient 3's binder prescription was maintained at 6 PhosLo® pills per day. For the 6 month study period, average serum P was 5.3 mg/dL. As also illustrated in FIG. 4, serum P fell within recommended guidelines for the study period. The average PPR for Patient 3 during the study period was 11.8, which was within the recommended range. Although the number of P binder pills was not increased, serum P decreases may be attributed to increased compliance with diet and prescriptions as a result of additional education and monitoring provided by the study program.

Example 4

Figure 5:
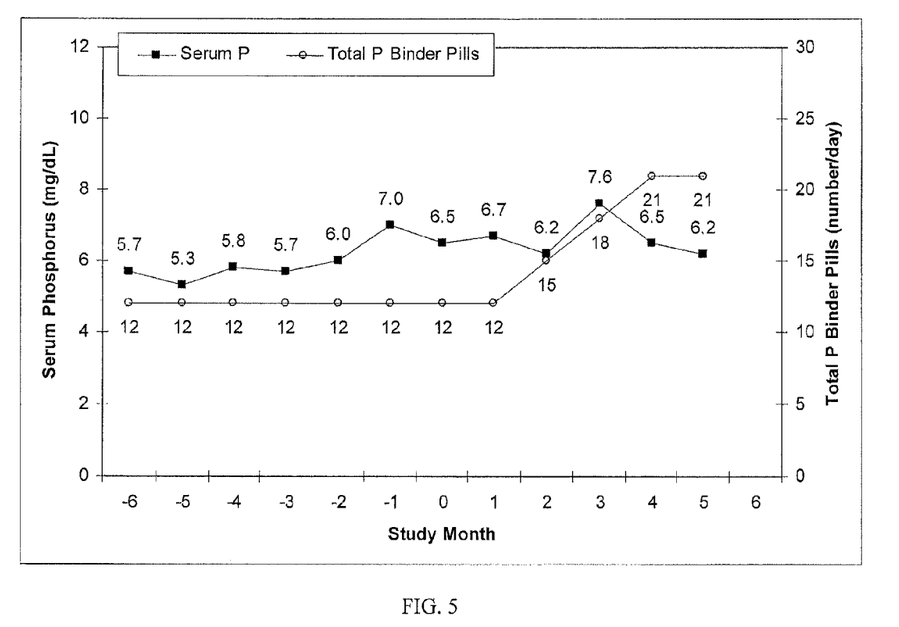
FIG. 5 is a graph of serum phosphorus concentration and number of prescribed phosphorus binder pills for Patient 4.

Patient 4 was a 63 year old diabetic, white male with a dialysis vintage of 40 months. Prior to use of the PPR, the 6-month, 3-month, and 1-month average serum P was 5.9, 6.2, and 7.0 mg/dL, respectively. All of these values are outside the recommended guidelines of 3.5-5.5 mg/dL. In the 6 months prior to the study, Patient 4 was prescribed 12 PhosLo® tablets per day. Once per month for 6 months (study months 0-5), input values were collected for the PPR and recommended binder prescription was calculated. As illustrated in FIG. 5, during the study period, Patient 4's binder prescription was increased from 12 steadily to 21 PhosLo® pills per day in an attempt to bring serum P level down within the recommended guidelines. For the 6 month study period, average serum P was 6.6 mg/dL. As illustrated in FIG. 5, serum P did not reach the recommended range. The average PPR for Patient 4 during the study period was 15.8, which is outside of the recommended range (8-14). Clinical staff were alerted to monitor patient compliance with P binder prescription and diet. Although the PPR can suggest a PhosLo® prescription to lower serum P, if patients are non-compliant with this prescription or recommended diet, serum P will not be lowered.

Example 5

Patient 5 had a dialysis treatment that was calculated to remove 547 mg of phosphorus per treatment (or 234 mg P per day) and PhosLo® prescription of 6 pills per day which would remove 150 mg of phosphorus. This translated to a daily dietary intake of 462 mg P. Patient 5 also had a PCR of 68.8 g/day, which would result in a PPR of 6.7. This PPR is below the acceptable range of 8-14 and would suggest that the low PPR may be a result of residual renal function. Patient 5 had a measured residual renal urea clearance of 3 mL/min. Using the relationship from FIG. 1, a residual renal clearance of 3 mL/min would correspond to a kidney phosphorus removal rate of 276 mg/day. If this additional phosphorus removal source is included in the total phosphorus (462+276 mg/day), then the calculated PPR is 12.3, which is within the acceptable range of 8-14.

Example 6

Patient 6 had a dialysis treatment that was calculated to remove 666 mg of phosphorus per treatment (or 285 mg P per day) and a recorded PhosLo® prescription of 15 pills per day which would remove 375 mg of phosphorus. This translated to a daily dietary intake of 756 mg P. Patient 6 also had a PCR of 52.4 g/day, which would result in a PPR of 14.4. This PPR is above the acceptable range of 8-14 and would suggest that Patient 6 is non-compliant with their PhosLo prescription and/or dietary guidelines. From a PhosLo® tracking calendar, Patient 6 records taking 3 PhosLo® pills per day. The actual number of PhosLo®) pills being taken resulted in a daily removal of 75 mg P per day. Adjusting the PPR calculation for this information, the daily dietary intake is calculated to be 456 mg P and the PPR is calculated to be 8.7. The PPR calculated from the actual number of PhosLo® pills per day is within the acceptable range of 8-14.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of identifying a patient who is non-compliant with a prescribed diet and/or a phosphate binder regimen over a defined time interval prior to a medical treatment in which phosphorus is removed from the patient, comprising:
    a) determining the patient's protein intake over said defined time interval;
    b) determining the amount of phosphorus removed from the patient during said defined time interval and removed by said medical treatment;
    c) calculating a ratio between the amount of phosphorus removed from the patient and the patient's protein intake over said defined time interval; and
    d) identifying a patient that is non-compliant with a prescribed diet and/or a phosphate binder regimen if the ratio is outside of an acceptable range.

2. The method of claim 1, in which determining the amount of phosphorus removed from the patient during said defined time interval and removed by said medical treatment includes:
    a) measuring the patient's serum phosphorus concentration before and after said medical treatment to determine the amount of phosphorus removed from the patient by said medical treatment;
    b) estimating the amount of phosphorus removed by the patient's kidneys during said defined time interval;
    c) determining the amount of phosphorus that would be removed from the patient by the prescribed phosphate binder regimen; and
    d) adding the amounts determined and estimated in steps a), b), and c).

3. The method of claim 1, wherein the medical treatment comprises dialysis treatment.

4. The method of claim 3, wherein estimating the amount of phosphorus removed by the patient's kidneys is based upon the patient's measured residual urea clearance.

5. The method of claim 1, wherein said phosphate binder regimen comprises ingestion of phosphate binder tablets.

6. The method of claim 3, wherein the defined time interval is the time interval between the end of one dialysis treatment and the beginning of the next subsequent dialysis treatment.

7. The method of claim 1, wherein determining the patient's protein intake includes an in vitro measurement of blood urea nitrogen concentration using an automated clinical chemistry analyzer.

8. The method of claim 2, wherein measuring the patient's serum phosphorus concentration includes an in vitro measurement using an automated clinical chemistry analyzer.

9. The method of claim 1, wherein the acceptable range is between about 8 and about 14.

10. A method of identifying a patient who is non-compliant with a prescribed diet and/or a phosphate binder regimen over a defined time interval comprising:
   a) determining the patient's protein intake;
   b) estimating the amount of phosphorus removed by the patient's kidneys from measured residual urea clearance;
   c) determining the amount of phosphorus that would be removed from the patient by the prescribed phosphate binder regimen;
   d) determining a total amount of phosphorus removed from the patient;
   e) calculating a ratio between the total amount of phosphorus removed from the patient and the patient's protein intake; and
   f) identifying a patient that is non-compliant with prescribed diet and/or phosphate binder regimen if the ratio is outside of an acceptable range.

11. The method of claim 10, wherein the defined time interval is the time interval between the end of one dialysis treatment and the beginning of the next subsequent dialysis treatment.

12. The method of claim 10, wherein the acceptable range is between about 8 and about 14.

13. A computer system for identifying a patient who is non-compliant with a prescribed diet and/or a phosphate binder regimen over a defined time interval prior to a medical treatment in which phosphorus is removed from the patient, the computer system comprising:
   a) a user input means for determining patient data from a user;
   b) a digital processor coupled to receive determined patient data from the input means, wherein the digital processor executes a modeling system in working memory, wherein the modeling system:
      i) determines the patient's protein intake over said defined time interval;
      ii) determines the amount of phosphorus removed from the patient during said defined time interval and removed by said medical treatment;
      iii) calculates a ratio between the amount of phosphorus removed from the patient and the patient's protein intake over said defined time interval; and
      iv) identifies a patient that is non-compliant with a prescribed diet and/or a phosphate binder regimen if the ratio is outside of an acceptable range; and
   c) an output means coupled to the digital processor, the output means provides to the user the ratio between the phosphorus removed from the patient and the patient's protein intake.

14. The computer system of claim 13, wherein the patient data includes blood urea nitrogen concentration and serum phosphorus concentration.

15. The computer system of claim 14, wherein the blood urea nitrogen concentration is measured in vitro using an automated clinical chemistry analyzer.

16. The computer system of claim 14, wherein the serum phosphorus concentration is measured in vitro using an automated clinical chemistry analyzer.

* * * * *

UNITED STATES PATENT AND TRADEMARK OFFICE
CERTIFICATE OF CORRECTION

| | | |
|---|---|---|
| PATENT NO. | : 8,822,225 B2 | Page 1 of 1 |
| APPLICATION NO. | : 13/499485 | |
| DATED | : September 2, 2014 | |
| INVENTOR(S) | : Frank A. Gotch et al. | |

It is certified that error appears in the above-identified patent and that said Letters Patent is hereby corrected as shown below:

On the title page of Patent No. 8,822,225, after item (65) and before item (51), please insert:

-- Related U.S. Application Data
(60) Provisional Application No. 61/277,935, filed on October 1, 2009. --

Signed and Sealed this
Ninth Day of December, 2014

Michelle K. Lee
*Deputy Director of the United States Patent and Trademark Office*